United States Patent [19]

Long

[11] Patent Number: 5,498,638
[45] Date of Patent: Mar. 12, 1996

[54] STAGED HYDROCARBON SYNTHESIS PROCESS

[75] Inventor: David C. Long, Boonton, N.J.

[73] Assignee: Exxon Research & Engineering Co., Florham Park, N.J.

[21] Appl. No.: 236,905

[22] Filed: Apr. 29, 1994

[51] Int. Cl.$^6$ .............................. C07C 27/00; C07C 1/00
[52] U.S. Cl. ........................... 518/706; 518/707; 518/715
[58] Field of Search ..................................... 518/706, 707, 518/715

[56] References Cited

U.S. PATENT DOCUMENTS 4,624,968  11/1986  Kim et al. .
5,028,634   7/1991  Fiato .
5,302,622   4/1994  Chaumette et al. .

Primary Examiner—Johann Richter
Assistant Examiner—John Peabody
Attorney, Agent, or Firm—J. Simon

[57] ABSTRACT

High conversion, substantially once-through hydrocarbon synthesis is achieved by reacting $H_2$ and CO in a first stage(s) in the presence of a non-shifting catalysts, separating liquid products and reacting the remaining gas streams in the presence of hydrocarbon synthesis catalysts having shifting activity.

9 Claims, 1 Drawing Sheet

STAGED HYDROCARBON SYNTHESIS PROCESS

FIELD OF THE INVENTION

This invention relates to a hydrocarbon synthesis process that substantially eliminates the necessity for recycling products, More particularly, this invention relates to a highly efficient, once through hydrocarbon synthesis process wherein the synthesis is effected first over a non-shifting catalyst and then over a shifting catalyst.

BACKGROUND OF THE INVENTION

Hydrocarbon synthesis, also known as Fischer-Tropsch, processes involve the catalytic hydrogenation of synthesis gas, hydrogen and carbon monoxide, to form higher hydrocarbons, e.g., $C_2+$, but preferably $C_5+$ materials. The synthesis gas feed can also contain small amounts of $CH_4$ and $CO_2$ as carry overs from the synthesis gas manufacturing step.

The hydrocarbon synthesis reaction produces hydrocarbons and water, and at reaction conditions the water product can readily react with CO in the water gas shift reaction

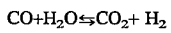

$$CO+H_2O \rightleftharpoons CO_2+ H_2$$

to produce $CO_2$, a deleterious side reaction since the objective of the process is the production of higher hydrocarbons from $H_2$ and CO. By the use of so-called "non-shifting" catalysts, e.g., cobalt on titania, silica, or alumina which have low selectivity for $CO_2$; the water gas shift reaction is largely suppressed.

Iron based hydrocarbon synthesis catalysts usually promote the water gas shift reaction and have a high selectivity to $CO_2$. Thus, by virtue of the relatively high CO concentration in the synthesis gas feed and the fact that water is produced in the synthesis process as hydrogen is reacted, the water gas shift reaction becomes important. The shift reaction can, however, be suppressed if the feed contains higher amounts of $CO_2$ relative to CO, and $CO_2$ is known to be added to $H_2+$ CO synthesis gas feeds for hydrocarbon synthesis. Synthesis gas feeds can contain up to 10% $CO_2$, that is, about 0.1–10% $CO_2$.

The invention described herein makes use of non-shifting catalysts to convert a large portion of the CO in the synthesis gas to desired hydrocarbons, resulting in an enrichment of the gas phase $CO_2$ concentration, followed by the use of a shifting catalyst wherein the presence of $CO_2$ suppresses further shifting and results in exceedingly high overall CO conversions in the order of 95+%, preferably 97% or greater. These CO conversion levels substantially eliminate the need for any recycling of hydrocarbon synthesis products back to the hydrocarbon synthesis reactors, thereby eliminating the need for costly recompression and treatment of recycled gases for removing oxygenated products, e.g., alcohols, aldehydes, that may poison or suppress the synthesis reaction.

SUMMARY OF THE INVENTION

In accordance with this invention, a substantially once through hydrocarbon synthesis process is provided wherein in a first stage or stages hydrogen and carbon monoxide are reacted at reaction conditions in the presence of a substantially non-shifting catalyst and the product of this reaction, after removing condensibles, is further reacted in a second stage or stages, at reaction conditions in the presence of a catalyst having substantial shift activity.

The feed to the first stage or stages contains hydrogen and carbon monoxide in a 1.5:1 to 2.5:1 mol ratio, preferably 1.9:1 to 2.3:1 mol ratio, and $CO_2$ in the range of 1.0–10 mol %, preferably 5–10 mol %. The product of the reaction over the non-shifting catalyst contains unreacted hydrogen and carbon monoxide, $C_2+$ hydrocarbons, oxygenated products such as alcohols, e.g., methanol, aldehydes, water, $CO_2$, methane and some inerts such as nitrogen. After removing condensible products, the remaining vapor feed comprising hydrogen, carbon monoxide, uncondensed oxygenated products, $CO_2$ and water is reacted in a subsequent hydrocarbon synthesis stage or stages in the presence of a shifting catalyst and produces higher hydrocarbons, including olefins, in an olefin:paraffin ratio of about 1.5:1 to 4:1, the lower ratios being favored for higher hydrocarbons, the higher ratios being favored at lower carbon numbers.

The hydrogen to carbon monoxide ratio entering the second or shifting stage(s) will have essentially the same mol ratio at that entering the first or non-shifting stage since the stoichiometric reaction ratio for the Fischer-Tropsch synthesis is approximately 2.1:1. However, there will be less total gas entering the second stage(s) and, therefore, the relative concentration of $CO_2$ in the second stage(s) will be greater than that in the first stage(s).

This once through process, i.e., substantial absence of recycle of hydrocarbon synthesis products to the hydrocarbon synthesis reactions, results in overall CO conversion to hydrocarbon of at least 95+%, and preferably 97+%.

DETAILED DESCRIPTION

Figure 1:
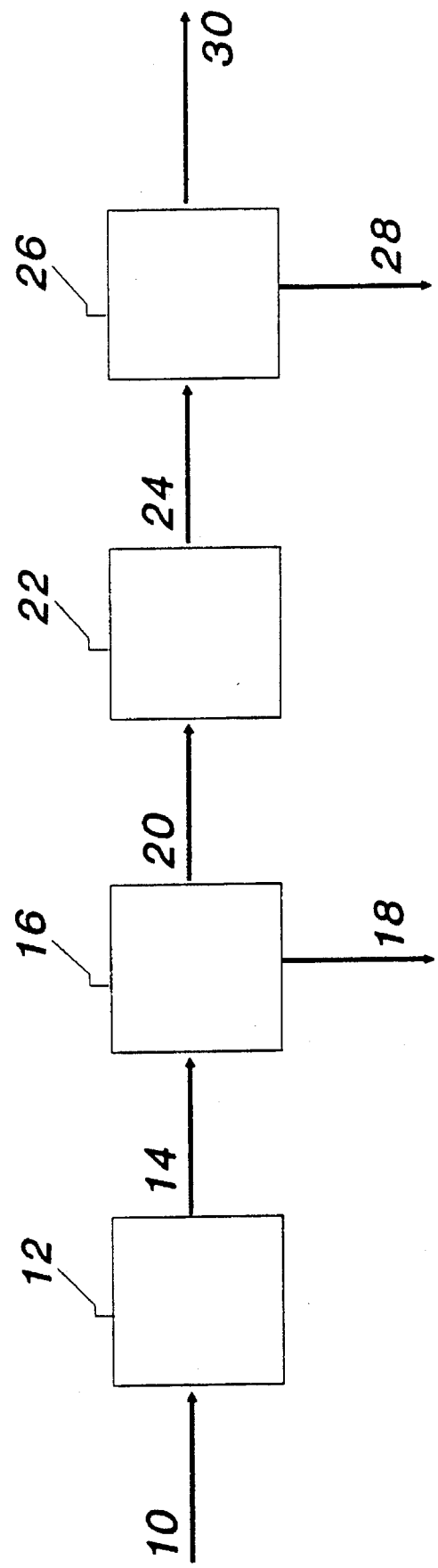
FIG. 1 is a block schematic depicting the process of this invention.

Details of the process can be easily obtained by reference to the drawing in which synthesis gas feed in line 10 enters reaction stages 12 in which a non-shifting catalyst is present. The hydrocarbon synthesis process is effected at temperatures ranging from about 175° C. to about 450° C., preferably about 190° C. to 250° C. and pressures of about 1–100 bar, preferably 20–40 bar. The non-shifting catalyst can be any of the well known hydrocarbon synthesis catalysts such as cobalt or ruthenium supported on a Group IIIA, IVA, or VA inorganic refractory oxide material. Promoter materials can also be present such as Group IA, IB, or IIA metals. Preferred catalysts are cobalt on titania, silica, or alumina, preferably titania. Preferred promoters are ruthenium, rhenium, cerium, or hafnium, particularly ruthenium and rhenium, most particularly rhenium. These materials are prepared in well known ways, see for example U.S. Pat. Nos. 4,637,993, 4,717,702, 4,477,595, 4,663,305, 4,822,824, 5,036,032, 5,140,050, 5,292,705.

The reaction in the presence of the non-shifting catalyst can take place in one or more stages, normally resulting in at least about 80+% CO conversion, preferably at least about 85% conversion, more preferably at least about 90% CO conversion. The product of the non-shifting reaction is removed via line 14 and transferred to separator(s) 16 where condensible products are removed from the system by well known means, e.g., cooling and liquid phase separation. The liquid products separated contain $C_5+$ hydrocarbons, water, oxygenated compounds and small amounts of dissolved gases.

The remaining vapor in line 20 is then transported to subsequent hydrocarbon synthesis stages 22 in which shifting type catalysts are present. The vapor stream 20 contains unreacted $H_2$ and CO as well as $CO_2$, $H_2O$, inerts, and uncondensed oxygenated products. This stream contains substantially less CO than the feed to the first stages (non-shifting catalysts) and the ratio of $CO_2$ to CO is greater than 2, preferably greater than 4. Sufficient hydrogen must also be present in the vapor stream to react with CO and $CO_2$ to form hydrocarbon products. Thus, the mole ratio of hydrogen to CO+ $CO_2$ is at least 0.2:1, preferably at least 0.25:1. Additional or make up hydrogen, if necessary, may be added to stages 22 by means not shown.

Reaction conditions in these subsequent shifting catalyst stages are similar to reactions conditions in the first, non-shifting catalyst stages, although in the absence of recompression pressures will be at the lower end of the range, e.g., 10–35 bar, and will be reflective of the degree of CO conversion in the first stages, e.g., temperature of 220–350° C., SHSV 200–2000, dry feed, e.g., $H_2O$<5 vol %.

Reaction conditions will, of course, favor maximum CO conversion with lowest selectivity to methane and $CO_2$. Selectivity can be defined as moles methane or $CO_2$ produced per mole CO converted.

Reaction product is withdrawn via line 24 and sent to separator(s) 26 where liquid products are withdrawn via line 28 and a tail gas is recovered in line 30. The tail gas is substantially devoid of reactive molecules and may be used as a fuel gas or flared. In one embodiment it may be recycled to the synthesis gas manufacturing step and used as a fuel.

The shifting catalysts in stage(s) 22 are preferably iron based but also may be those disclosed in Catalysis Science & Technology; Anderson, J.R. Bondart, M. ed. Vol. 1, 1981, p. 175 et seq.

Hydrocarbon synthesis processes can be carried out in fixed bed, fluid bed, and bubble column reactors—all of which are well known to the art and fully described in available literature. It is not important to this invention whether reactors in the first stages are the same or different, although slurry type, bubble column reactors are now usually preferred. For the second (shifting) stage(s), due to the low concentration of reactant gases, substantially plug flow reactor(s) (e.g., fixed or fluid bed) are preferred.

The process of this invention can be illustrated by the following example:

A synthesis gas feed containing hydrogen and carbon monoxide in the ratio of 2.25:1 is reacted to convert 95% of the CO using a cobalt on titania catalyst. The tailgas from this reaction flows to a second stage reactor containing an iron based catalyst (shifting catalyst). Due to the shift reaction, there is a net disappearance of $CO_2$ in the second stage reactor, and an increase in hydrocarbon yield compared to a non-shifting reactor. Table 1 shows the material balances for both shifting and non-shifting second stage reactor simulations. Total ($CO_2$+ CO) conversion increases from 12% for the non-shifting case to 18.4% for the shifting second stage. Hydrocarbon and alcohol yield increases from 223 moles/hour to 344 moles/hour for the shifting case.

TABLE 1

Reactor Simulation Results

| | | Stage 2 Product | |
|---|---|---|---|
| | Stage 2 Feed | Shifting Catalyst | Non-shifting |
| Component Rates, Moles/Hr | | | |
| $H_2$ | 11584 | 3021 | 6781 |
| CO | 2823 | 564 | 524 |
| $CO_2$ | 16324 | 15065 | 16326 |
| $H_2O$ | 113 | 4887 | 2400 |
| Hydrocarbon + Alcohol | 13701 | 14045 | 13924 |
| Inert | 2434 | 2434 | 2434 |
| Moles Converted | | | |
| CO | | 2259 | 2299 |
| $CO_2$ | | 1259 | –2 |
| Total | | 3518 | 2297 |
| % (CO + $CO_2$) Converted | | 18.4 | 12.0 |
| Hydrocarbon + Alcohol Yield, Moles/Hr | | 344 | 223 |

What is claimed is:

1. A once through hydrocarbon synthesis process which comprises reacting in a first stage or stages, a feed comprising hydrogen and carbon monoxide, and optionally $CO_2$, in the presence of a non-shifting hydrocarbon synthesis catalyst containing cobalt or ruthenium, recovering the product therefrom, condensing liquids from the product and reacting the remaining gases in a subsequent stage or stages in the presence of a hydrocarbon synthesis catalyst having shifting activity, and recovering the products therefrom.

2. The process of claim 1 wherein the $H_2$:(CO+$CO_2$) ratio entering the subsequent stage(s) is at least about 0.2:1.

3. The process of claim 1 wherein the CO conversion in the non-shifting stage(s) is at least about 80%.

4. The process of claim 1 wherein the CO conversion in the shifting stage(s) is at least about 80%.

5. The process of claim 1 wherein the first stage(s) catalyst comprises cobalt and the second stage(s) catalyst comprises iron.

6. The process of claim 1 wherein the feed contains up to about 10 vol % $CO_2$.

7. The process of claim 6 wherein the $CO_2$ concentration of the feed is 1–10 mol %.

8. The process of claim 1 wherein the reaction conditions in the first and subsequent stage(s) include temperatures of 175–450° C., pressures of 1–100 bar and $H_2$:CO ratios of about 1.5:1 to 2.5:1.

9. The process of claim 1 wherein the CO conversion is at least about 95%.

* * * * *